United States Patent [19]

Child et al.

[11] 4,006,234
[45] Feb. 1, 1977

[54] SUBSTITUTED 2-BENZOFURANYL PROPENONES AS ANTI-TUBERCULAR AGENTS

[75] Inventors: Ralph Grassing Child, Pearl River, N.Y.; Raymond George Wilkinson, Montvale; Andrew Stephen Tomcufcik, Old Tappan, both of N.J.

[73] Assignee: American Cyanamid Company, Stamford, Conn.

[22] Filed: Dec. 29, 1975

[21] Appl. No.: 645,065

Related U.S. Application Data

[62] Division of Ser. No. 534,029, Dec. 18, 1974, Pat. No. 3,931,157.

[52] U.S. Cl. .............................. 424/251; 424/273; 424/244
[51] Int. Cl.² ..................................... A61K 31/505
[58] Field of Search ................... 424/251, 273, 244

[56] References Cited

UNITED STATES PATENTS

| 3,414,580 | 12/1968 | Hohn | 260/240 G X |
| 3,743,639 | 7/1973 | Schlapfev | 260/240 D |
| 3,859,279 | 1/1975 | Fothevgill et al. | 260/346.2 R X |
| 3,882,149 | 5/1975 | Dusza et al. | 260/346.2 R |

Primary Examiner—Jerome D. Goldberg
Attorney, Agent, or Firm—Neal O. Willmann

[57] ABSTRACT

The preparation of 2-(1,3-diazacycloalkenyl)-2-hydrazones of 1-(substituted 2-benzofuranyl)-3-(substituted aryl)-2-propen-1-ones is described. These compounds are useful as anti-tubercular agents in warm blooded animals.

4 Claims, No Drawings

SUBSTITUTED 2-BENZOFURANYL PROPENONES AS ANTI-TUBERCULAR AGENTS

CROSS-REFERENCE TO RELATED APPLICATIONS

This application is a divisional of our prior application Ser. No. 534,029, filed Dec. 18, 1974, now U.S. Pat. No. 3,931,157, issued Jan. 6, 1976. It is also related to our prior application Ser. No. 437,549, filed Jan. 20, 1974, now U.S. Pat. No. 3,931,152, issued Jan. 6, 1976, which is directed to the preparation of 2-(1,3-diazacycloalkenyl)-2-hydrazones of substituted chalcones.

DESCRIPTION OF THE INVENTION

The substituted benzofuranyl compounds of the present invention may be illustrated by the following formula:

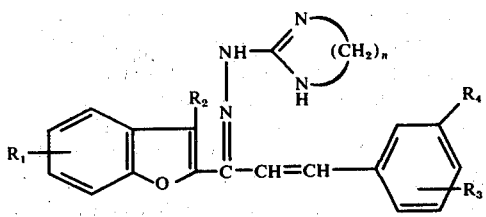

wherein $R_1$ and $R_3$ may be the same or different and are selected from the group consisting of hydrogen, chloro, bromo, fluoro, $C_1$–$C_4$ alkoxy, $C_1$–$C_4$ alkyl, phenyl, and $C_1$–$C_4$ alkyl thio, $R_2$ is selected from the group consisting of hydrogen, $C_1$–$C_4$ alkyl and phenyl, $R_4$ is hydrogen, $C_1$–$C_4$ alkyl or chloro, and when $R_3$ and $R_4$ are present on adjacent carbon atoms, they may represent —O—$CH_2$—O, $n$ is 2, 3 or 4, or an acid addition salt thereof.

The acid addition salts may be for example hydrochloride, hydrobromide, hydroiodide, sulfate, nitrate, phosphate, hydrochloride n-propanolate, etc.

The present compounds are usually crystalline solids and in the form of their salts are somewhat soluble in water.

One method of preparing compounds of the present invention is illustrated by the following reaction:

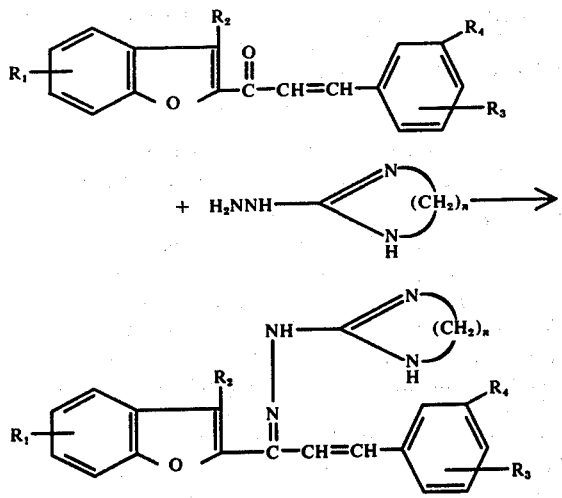

wherein $R_1$, $R_2$, $R_3$, $R_4$ and $n$ are as defined hereinbefore and whereby the appropriately substituted 2-propen-1-one is boiled with an equivalent quantity of the hydrazine in a suitable solvent such as propanol and in which there is present from slightly over one to two or more equivalents of a strong acid such as hydrochloric acid. The boiling is continued for approximately 1 to 2 hours during which time the volume is allowed to reduce to approximately half. The product may be removed directly from the cooled reaction medium as the acid salt or as the free base following dilution with water and basification.

The reaction is carried out in a hydrophilic solvent such as ethanol, n-propanol, butanol, dioxane, 2-methoxyethanol, etc., at a temperature which may vary from about 70° to 140° C. The time for completing the reaction may vary from about 0.5 to 16 hours. As catalyst, a small portion of hydrohalic acid may be added to the reaction mixture.

The compounds of this invention are active against Mycobacterium tuberculosis H37Rv infections in mice when tested in accordance with the following procedure.

Carworth Farms CF1 female white mice, 4 to 6 weeks old, weighing 17 to 22 g. are infected with Mycobacterium tuberculosis H37Rv by intravenous administration of 0.2 ml. of a buffered saline suspension containing approximately 1.5 mg./ml. wet weight of a 12 to 14 day culture of the test organism grown on Sauton's agar medium. Routinely 200–300 mice are given this standard infection and then segregated in a random manner into cages each of which holds five or 10 mice. Four groups of five mice each are retained as untreated controls and the remaining mice are used to ascertain activity of the compounds under test. During a 1 year experience with this test, the standard infection defined above caused a 99.5% mortality, in that 756 of the 760 infected untreated control mice died within 28 days, the normal period of the test.

A measured amount of each compound to be tested is administered orally, incorporated in a Standard Diet to groups of infected mice for 14 days, after which the mice are fed untreated Standard Diet. Control animals receive untreated Standard Diet for the entire test period and all animals are allowed to feed at will. Tests are terminated 28 days after the day of infection. A compound is judged active if it either saves one or two of two mice in a test group or two or more of five mice in a test group in two tests, or prolongs average survival time by 4 or more days compared to untreated controls.

The Standard Diet used in this test procedure is a commercial feed designated for laboratory mice and rats composed of the following ingredients: Animal liver meal, fish meal, dried whey, corn and wheat flakes, ground yellow corn, ground oat groats, dehulled soybean meal, wheat germ meal, wheat middlings, can molasses, dehydrated alfalfa meal, soybean oil, brewers' dried yeast, irradiated dried yeast (source of Vitamin $D_2$), riboflavin, niacin, calcium pantothenate, choline chloride, Vitamin A palmitate, D-activated animal sterol, α-tocopherol, dicalcium phosphate, thiamine hydrochloride, menadione sodium bisulfite (source of Vitamin K activity), salt and traces of maganous oxide, copper sulfate, iron carbonate, potassium iodate, cobalt sulfate and zinc oxide. This commercial feed has a guaranteed analysis of a minimum of 24.0% crude protein, a minimum of 4.0% crude fat and a maximum of 4.5% crude fiber and is sold under the trademark Wayne Lab-Blox by Allied Mills Inc., Chicago, Ill.

The following Table shows the activity of representative compounds of this invention against *Mycobacterium tuberculosis* infections in mice.

TABLE

| Compound of Example | Percent of Compound in Diet | Alive/Total Mice Tested 28 Days After Infection |
| --- | --- | --- |
| 5  | 0.05   | 5/5 |
|    | 0.0125 | 2/5 |
| 6  | 0.05   | 2/5 |
| 7  | 0.05   | 4/5 |
| 8  | 0.05   | 5/5 |
|    | 0.0125 | 2/5 |
| 9  | 0.05   | 5/5 |
|    | 0.0125 | 2/5 |
| 10 | 0.05   | 3/5 |
| 11 | 0.05   | 5/5 |
|    | 0.0125 | 3/5 |
| 12 | 0.05   | 4/5 |
| 13 | 0.05   | 4/5 |
| 14 | 0.05   | 4/5 |
|    | 0.0125 | 2/5 |
| 15 | 0.05   | 4/5 |
| 16 | 0.05   | 5/5 |
|    | 0.0125 | 3/5 |
| 17 | 0.05   | 5/5 |
| 18 | 0.05   | 2/5 |
| 19 | 0.05   | 3/5 |
| 20 | 0.05   | 5/5 |
|    | 0.0125 | 2/5 |
| 21 | 0.05   | 4/5 |
| 22 | 0.05   | 5/5 |
| 23 | 0.05   | 2/5 |
| 24 | 0.05   | 4/5 |
|    | 0.0125 | 2/5 |
| 25 | 0.05   | 2/5 |
| 27 | 0.05   | 4/5 |
| 28 | 0.05   | 3/5 |
| 29 | 0.05   | 2/5 |
| 30 | 0.05   | 3/5 |
| 31 | 0.05   | 4/5 |
| 32 | 0.05   | 5/5 |
| 36 | 0.05   | 4/5 |

Compositions containing as the active component a 2-(1,3-diazacycloalkenyl)-2-hydrazone of a 1-(substituted 2-benzofuranyl)-3-(substituted aryl)-2-propen-1-one of this invention may be administered to warm blooded animals orally, or parenterally if desired, and when so administered, may be considered as an agent for the therapeutic treatment of tuberculosis infections in daily doses ranging from about 10 mg. to about 100 mg. per kilogram of body weight. The dose regimen can be adjusted to provide optimum therapeutic response. Thus, for example, several smaller doses may be administered daily, or the dose may be reduced or increased proportionately as indicated by the requirements or the particular therapeutic situation.

The active compounds of this invention may be incorporated with pharmaceutically acceptable carriers such as excipients and used, for example, in the form of tablets, dragees, capsules, suppositories, liquids, elixirs, emulsions, suspensions or the like. Such compositions and preparations should contain at least 5% active component. The percentage in the compositions and preparations may, of course, be varied and may conveniently be between 10 and 60% or more of the weight of the unit. The amount of compound in such therapeutically useful composition or preparation is such that a suitable dosage will be obtained. Preferred compositions or preparations according to the present invention are prepared so that a dosage unit form contains between about 10 and about 500 mg. of the active compound. In addition to the therapeutic compound there may be present excipients, binders, fillers and other therapeutically inert ingredients necessary in the formulation of the desired pharmaceutical preparation.

SPECIFIC DISCLOSURE

The following examples describe the preparation of intermediates and the use of these intermediates in the preparation of the products of this invention.

EXAMPLE 1

Preparation of Starting Material
2-Hydrazino-2-imidazoline hydrochloride

A 33.0 g. (0.135 mole) portion of 2-methylthio-2-imidazoline hydroiodide is dissolved in 300 ml. of water and treated with 8 ml. (0.16 mole) of hydrazine hydrate. The mixture is stirred at room temperature for 20 hours and then taken to dryness under reduced pressure. The residue is dissolved in 250 ml. of water and again taken to dryness under reduced pressure. The residue is redissolved in 250 ml. of water and added to a mixture of 250 ml. of water, 25 ml. of concentrated hydrochloric acid and 25 g. of silver oxide. The resulting mixture is stirred on a steam bath for 4 hours and then filtered. The filtrate is reduced to dryness under reduced pressure. The residue is dissolved in 300 ml. of ethanol and 20 ml. of water at the boil, clarified and cooled at −10° C. The precipitate is collected, washed with ethanol and ether and dried at 60° C. and then 110° C. under reduced pressure. Yield 11.6 g., m.p. 177°–180° C.

Analysis calculated for $C_3H_8N_4 \cdot HCl$: C, 26.38; H, 6.64; N, 41.02; Cl, 25.96. Found: C, 26.06; H, 6.38; N, 40.13; Cl, 25.59.

EXAMPLE 2

Preparation of Starting Material
2-Hydrazino-4-methyl-2-imidazoline dihydrochloride Eighty grams of 4-methyl-2-methylthio-2-imidazoline hydroiodide, 20 ml. of 100% hydrazine hydrate and 250 ml. of ethanol are combined and heated under reflux for 16 hours. Removal of solvent leaves a glassy solid which resists attempts at crystallization. Conversion to the hydrochloride salt is similarly unsuccessful. However, solution of the solid in n-propanol followed by addition of an equivalent of anhydrous hydrogen chloride in the same solvent gives the dihydrochloride salt, melting at 128°–131° C.

Analysis calculated for $C_4H_{10}N_4 \cdot 2HCl$: C, 25.68; H, 6.47; N, 29.95; Cl, 37.90. Found: C, 24.96; H, 6.25; N, 30.04; Cl, 37.39.

EXAMPLE 3

Preparation of Starting Material
2-Hydrazino-1,4,5,6-tetrahydropyrimidine hydrochloride A 35 g. (0.3 mole) portion of 2-mercapto-1,4,5,6-tetrahydropyrimidine in 500 ml. of ethanol is stirred as 30 ml. of methyl iodide is added. The mixture is refluxed with stirring for 8 hours. A 25 ml. portion of concentrated hydrochloric acid and 48 g. of silver chloride are added and the mixture is stirred at reflux for 1 hour and then allowed to stand at room temperature for 2.5 days. The mixture is refluxed for 5 more hours, clarified and the filtrate is reduced to an oil under reduced pressure. The oil is dissolved in 100 ml. of boiling isopropanol and then cooled at −10° C. A 300 ml. portion of acetone is added and the mixture is kept at −10° C. The precipitate which forms is collected, washed with acetone and dried at 60° C. under reduced pressure. This solid is dissolved in 150 ml. of ethanol, treated with 8 ml. (0.16 mole) of hydrazine hydrate and stirred at reflux for 6 hours. The mixture is filtered hot and cooled at −10° C. The mixture is diluted with 150 ml. of ether and stored at −10° C. The precipitate which forms is collected, washed with 150 ml. of ether and dried under reduced pressure at 60° C. Yield 17.9 g., m.p. 191°–192° C.

Analysis calculated for $C_4H_{10}N_4 \cdot HCl$: C, 31.90; H, 7.36; N, 37.20; Cl, 23.54. Found: C, 32.14; H, 7.38; N, 37.98; Cl, 22.89.

EXAMPLE 4

Preparation of Starting Material 2-Hydrazino-4,5,6,7-tetrahydro-1H-1,3-diazepine hydrochloride A 38.5 g. (0.14 mole) portion of 2-methylthio-4,5,6,7-tetrahydro-1H-1,3-diazepine hydroiodide is slurried in a mixture of 500 ml. of water and 40 g. (0.3 mole) of silver chloride. The mixture is stirred on a steam bath for 16 hours. The mixture is filtered and the filtrate is taken to dryness under reduced pressure. The residue is dissolved in 150 ml. of ethanol to which is added 7 ml. (0.14 mole) of hydrazine hydrate. The mixture is refluxed for 3 hours, clarified and cooled at −10° C. A 150 ml. portion of ether is added. The precipitate which forms is collected, washed with 150 ml. of ether and dried at 60° C. under reduced pressure yielding 19.4 g., m.p. 192°–193° C.

Analysis calculated for $C_5H_{12}N_4 \cdot HCl$: C, 36.47; H, 7.96; N, 34.03; Cl, 21.53. Found: C, 36.23; H, 8.07; N, 34.05; Cl, 21.49.

EXAMPLE 5

Preparation of the 4,5,6,7-Tetrahydro-1H-1,3-diazepin-2-ylhydrazone of 1-(2-Benzofuranyl)-3-(p-chlorophenyl)-2-propen-1-one A mixture of 5.66 g. of 1-(2-benzofuranyl)-3-(p-chlorophenyl)-2-propen-1-one, prepared from p-chlorobenzaldehyde and 2-acetylbenzofuran in methanol and a trace of alkali, and 3.3 g. of 2-hydrazino-4,5,6,7-tetrahydro-1H-1,3-diazepine hydrochloride in 100 ml. of n-propanol containing 3 drops of concentrated hydrochloric acid is heated to boiling and allowed to concentrate to 50 ml. over the course of 1 hour. The cooled solution is diluted with 3 volumes of water and basified with saturated sodium bicarbonate solution. The formed oil is washed three times with water by decantation and then boiled in 100 ml. of methanol and cooled yielding 3.4 g. of pale yellow solid, m.p. 178°–180° C.

Analysis calculated for $C_{22}H_{21}ClN_4O$: C, 67.25; H, 5.39; N, 14.26; Cl, 9.02. Found: C, 66.90; H, 5.41; N, 14.16; Cl, 9.29.

EXAMPLE 6

Preparation of the 4,5,6,7-Tetrahydro-1H-1,3-diazepin-2-ylhydrazone of 1-(2-Benzofuranyl)-3-(p-fluorophenyl)-2-propen-1-one The procedure of Example 5 is followed, employing 5.32 g. of 1-(2-benzofuranyl)-3-(p-fluorophenyl)-2-propen-1-one and 3.3 g. of 2-hydrazino-4,5,6,7-tetrahydro-1H-1,3-diazepin hydrochloride. The addition of water and sodium bicarbonate solution gives an oil which is washed twice with water. The oil is taken up in 250 ml. of methanol. A yellow solid precipitates which is collected by filtration, washed with methanol and dried yielding 4.0 g., m.p. 160°–161° C.

Analysis calculated for $C_{22}H_{21}N_4OF$: C, 70.19; H, 5.62; N, 14.88. Found: C, 69.97; H, 5.68; N, 14.88.

The starting material, 1-(2-benzofuranyl)-3-(p-fluorophenyl)-2-propen-1-one is prepared by the reaction of 2-acetylbenzofuran and p-fluorobenzaldehyde in methanol solution in the presence of aqueous sodium hydroxide. This starting material melts at 110°–111° C.

EXAMPLE 7

Preparation of the 4,5,6,7-Tetrahydro-1H-1,3-diazepin-2-ylhydrazone of 1-(2-Benzofuranyl)-3-(p-bromophenyl)-2-propen-1-one . n-propanolate The procedure of Example 5 is followed, employing 6.5 g. of 1-(2-benzofuranyl)-3-(p-bromophenyl)-2-propen-1-one and 3.3 g. of 2-hydrazino-4,5,6,7-tetrahydro-1H-1,3-diazepine hydrochloride. The yellow solid is precipitated from methanol, collected and dried, yielding 5.5 g., m.p. 166°–168° C. as the n-propanolate.

Analysis calculated for $C_{22}H_{21}N_4OBr \cdot C_3H_8O$: C, 60.37; H, 5.88; N, 11.26. Found: C, 60.62; H, 4.77; N, 11.68.

The starting material, 1-(2-benzofuranyl)-3-(p-bromophenyl)-2-propen-1-one is prepared by the reaction of 2-acetylbenzofuran of Example 6 and p-bromobenzaldehyde in a methanol solution in the presence of aqueous sodium hydroxide. This starting material melts at 155°–156° C.

EXAMPLE 8

Preparation of the 4,5,6,7-Tetrahydro-1H-1,3-diazepin-2-ylhydrazone of 1-(2-Benzofuranyl-3-(3,4-methylenedioxyphenyl)-2-propen-1-one The procedure of Example 5 is followed, employing 5.85 g. of 1-(2-benzofuranyl)-3-(3,4-methylenedioxyphenyl)-2-propen-1-one and 3.3g. of 2-hydrazino-4,5,6,7-tetrahydro-1H-1,3-diazepine hydrochloride. The yellow solid is precipitated from methanol, collected and dried yielding 5.9 g., m.p. 185°–186° C.

Analysis calculated for $C_{23}H_{22}N_4O_3$: C, 68.64; H, 5.51; N, 13.92. Found: C, 68.33; H, 5.57; N, 13.88.

The starting material 1-(2-benzofuranyl)-3-(3,4-methylenedioxyphenyl)-2-propen-1-one is prepared by the reaction of 2-acetylbenzofuran of Example 6 and 3,4-(methylenedioxy)benzaldehyde in methanol solution in the presence of aqueous sodium hydroxide. The starting material melts at 158°–160° C.

EXAMPLE 9

Preparation of the 4,5,6,7-Tetrahydro-1H-1,3-diazepin-2-ylhydrazone of 1-(2-Benzofuranyl)-3-m-tolyl-2-propen-1-one The procedure of Example 5 is followed, employing 5.2 g. of 1-(2-benzofuranyl)-3-m-tolyl-2-propen-1-one and 3.3 g. of 2-hydrazino-4,5,6,7-tetrahydro-1H-1,3-diazepine hydrochloride. The addition of water gives a mixture of a yellow solid and a hard gum. The yellow solid is recovered by filtration, washed with methanol and water and dried yielding the product, m.p. 138°–140° C.

Analysis calculated for $C_{23}H_{24}N_4O$: C, 74.17; H, 6.50; N, 15.04. Found: C, 73.82; H, 6.59; N, 14.98.

The starting material, 1-(2-benzofuranyl)-3-m-tolyl-2-propen-1-one is prepared by the reaction of 2-acetylbenzofuran of Example 6 and 3-m-tolualdehyde in methanol solution in the presence of aqueous sodium hydroxide. The starting material melts at 83°–84° C.

EXAMPLE 10

Preparation of the 4,5,6,7-Tetrahydro-1H-1,3-diazepin-2-ylhydrazone of 1-(2-Benzofuranyl)-3-(3,4-dichlorophenyl)-2-propen-1-one The procedure of Example 5 is followed, employing 6.32 g. of 1-(2-benzofuranyl)-3-(3,4-dichlorophenyl)-2-propen-1-one and 3.3 g. of 2-hydrazino-4,5,6,7-tetrahydro-1H-1,3-diazepine hydrochloride. The yellow solid is precipitated from methanol, collected and dried yielding 5.0 g., m.p. 164°–166° C.

Analysis calculated for $C_{22}H_{20}N_4OCl_2$: C, 61.83; H, 4.72; N, 13.11; Cl, 16.60. Found: C, 61.75; H, 4.70; N, 12.47; Cl, 16.91.

The starting material, 1-(2-benzofuranyl)-3-(3,4-dichlorophenyl)-2-propen-1-one is prepared by the reaction of 2-acetylbenzofuran and 3,4-dichlorobenzaldehyde in methanol solution in the presence of aqueous sodium hydroxide. The starting material melts at 148°–149° C.

EXAMPLE 11

Preparation of the (1,4,5,6-Tetrahydro-2-pyrimidinyl)hydrazone of 1-(5-Chloro-2-benzofuranyl)-3-(p-chlorophenyl)-2-propen-1-one A mixture of 6.34 g. of 1-(5-chloro-2-benzofuranyl)-3-(p-chlorophenyl)-2-propen-1-one and 3.0 g. of 2-hydrazino-1,4,5,6-tetrahydropyrimidine hydrochloride in 125 ml. of n-propanol containing 3 drops of concentrated hydrochloric acid is boiled for 2 hours and concentrated to 75 ml. The solution is cooled to 4° C. A solid which forms is removed by filtration and discarded. The filtrate is combined with 2 volumes of water and basified with excess sodium bicarbonate solution yielding a yellow gum which is also set aside. The mother liquor is combined with a third volume of water yielding a yellow solid which is collected and dried yielding 3.5 g., m.p. 163°–165° C.

Analysis calculated for $C_{21}H_{18}N_4OCl_2$: c, 61.03; H, 4.39; N, 13.56; Cl, 17.16. Found: C, 60.64; H, 4.32; N, 11.81; Cl, 17.21.

The starting material 1-(5-chloro-2-benzofuranyl)-3-(p-chlorophenyl)-2-propen-1-one is prepared by the reaction of 2-acetyl-5-chlorobenzofuran and 4-chlorobenzaldehyde in methanol solution in the presence of aqueous sodium hydroxide. The starting material melts at 171°–173° C.

EXAMPLE 12

Preparation of the (1,4,5,6-Tetrahydro-2-pyrimidinyl)hydrazone of 1-(7-Ethoxy-2-benzofuranyl)-3-(p-chlorophenyl)-2-propen-1-one A mixture of 9.81 g. of 1-(7-ethoxy-2-benzofuranyl)-3-(p-chlorophenyl)-2-propen-1-one and 4.52 g. of 2-hydrazino-1,4,5,6-tetrahydropyrimidine hydrochloride in 150 ml. of n-propanol containing 3 drops of concentrated hydrochloric acid is boiled for 2 hours, concentrated to 100 ml., cooled and then diluted with 4 volumes of water and basified with sodium bicarbonate solution. The yellow gum which forms is washed with water, drained dry, dissolved in 150 ml. of boiling methanol and cooled yielding a gum. The supernatant liquid is treated with 1 volume of water yielding a yellow solid, which is washed with water and dried. The gum and solid are combined and then recrystallized from 150 ml. of ethanol yielding the desired product as 3.4 g. of yellow-orange crystals, m.p. 168°–170° C.

Analysis calculated for $C_{23}H_{23}N_4O_2Cl$: C, 65.31; H, 5.48; N, 13.25; Cl, 8.38. Found: C, 65.1; H, 5.35; N, 13.04; Cl, 8.44.

The starting material 1-(7-ethoxy-2-benzofuranyl)-3-(p-chlorophenyl)-2-propen-1-one is prepared by the reaction of 7-ethoxy-2-acetylbenzofuran and p-chlorobenzaldehyde in methanol solution in the presence of aqueous sodium hydroxide. The starting material melts at 125°–127° C.

EXAMPLE 13

Preparation of the (1,4,5,6-Tetrahydro-2-pyrimidinyl)hydrazone of 1-(6-Methoxy-2-benzofuranyl)-3-(p-chlorophenyl)-2-propen-1-one The procedure of Example 5 is followed, employing 6.26 g. of 1-(6-methoxy-2-benzofuranyl-3-(p-chlorophenyl)-2-propen-1-one and 3.0 g. of 2-hydrazino-1,4,5,6-tetrahydropyrimidine hydrochloride. The cooled n-propanol solution is basified with saturated sodium bicarbonate solution and diluted with 5 volumes of water, yielding a dark gum. This gum is washed with water and then recrystallized from 350 ml. of methanol yielding 3.4 g. of yellow crystals, m.p. 173°–175° C.

Analysis calculated for $C_{22}H_{21}N_4O_2Cl$: C, 64.62; H, 5.18; Cl, 8.67; N, 13.70. Found: C, 64.93; H, 5.37; Cl, 8.53; N, 13.54.

The starting material 1-(6-methoxy-2-benzofuranyl)-3-(p-chlorophenyl)-2-propen-1-one is prepared by the reaction of 2-acetyl-6-methoxybenzofuran and 4-chlorobenzaldehyde in methanol solution in the presence of aqueous sodium hydroxide. The starting material melts at 180°–182° C.

EXAMPLE 14

Preparation of the 2-Imidazolin-2-ylhydrazone of 1-(5-chloro-2-benzofuranyl)-3-(p-chlorophenyl)-2-propen-1-one The procedure of Example 5 is followed, employing 3.2 g. of 1-(5-chloro-2-benzofuranyl)-3-(p-chlorophenyl)-2-propen-1-one and 1.73 g. of 2-hydrazino-2-imidazoline hydrochloride. The n-propanol solution is cooled, concentrated to 50 ml. and filtered. The filtrate is basified with saturated sodium bicarbonate solution and diluted with 3 volumes of water yielding a yellow-green gummy solid. This solid is mixed with 50 ml. of n-propanol and filtered. The filtrate is added to 2 volumes of water. A yellow solid forms which is collected and dried yielding 3.0 g., m.p., 106°–108° C.

Analysis calculated for $C_{20}H_{16}N_4OCl_2$: C, 60.15; H, 4.04; N, 14.03; Cl, 17.76. Found: C, 59.51; H, 4.26; N, 12.16; Cl, 17.31.

EXAMPLE 15

Preparation of the (1,4,5,6-Tetrahydro-2-pyrimidinyl)hydrazone of 1-(5-Chloro-2-benzofuranyl)-3-(p-methoxyphenyl)-2-propen-1-one hydrochloride A 4.70 g. portion of 1-(5-chloro-2-benzofuranyl)-3-(p-methoxyphenyl)-2-propen-1-one and 2.40 g. of 2-hydrazino-1,4,5,6-tetrahydropyrimidine hydrochloride in a mixture of 60 ml. of ethanol and 40 ml. of chloroform containing 3 drops of concentrated hydrochloric acid is boiled for 80 minutes yielding a clear yellow solution to which n-propanol is added to replace evaporated solvent. The solution is concentrated under reduced pressure to produce a gum. The gum is dissolved in 20 ml. of benzene and ether is added which on trituration produces a yellow solid. This solid is recrystallized from ethanol yielding 3.89 g. of pale yellow crystals, m.p. 224°–226° C.

Analysis calculated for $C_{22}H_{21}N_4O_2Cl$ . HCl: C, 59.3; H, 5.0; N, 12.6; Cl, 15.9. Found: C, 58.9; H, 5.1; N, 12.4; Cl, 15.8.

The starting material, 1-(5-chloro-2-benzofuranyl)-3-(p-methoxyphenyl)-2-propen-1-one is prepared by the reaction of 5-chloro-2-benzofuranyl methyl ketone and p-anisaldehyde in methanol solution in the presence of aqueous sodium hydroxide. The starting material melts at 164°–167° C.

EXAMPLE 16

Preparation of the (1,4,5,6-Tetrahydro-2-pyrimidinyl)hydrazone of 1-(5-Bromo-2-benzofuranyl)-3-(p-chlorophenyl)-2-propen-1-one The procedure of Example 5 is followed, employing 7.5 g. of 1-(5-bromo-2-benzofuranyl)-3-(p-chlorophenyl)-2-propen-1-one and 3.12 g. of 2-hydrazino-1,4,5,6-tetrahydropyrimidine hydrochloride. The concentrated n-propanol solution is basified with saturated sodium bicarbonate solution and diluted with 2 volumes of water which produces a yellow gum. The gum is washed twice with water, dissolved in 200 ml. of n-propanol filtered and cooled producing 5.3 g. of hard orange grains, m.p. 190°–192° C.

Analysis calculated for $C_{21}H_{18}N_4OBrCl$: C, 55.10; H, 3.96; N, 12.24; Br, 17.46; Cl, 7.75. Found: C, 54.78; H, 4.16; N, 12.13; Br, 15.92; Cl, 8.30.

The starting material 1-(5-bromo-2-benzofuranyl)-3-(p-chlorophenyl)-2-propen-1-one is prepared by the reaction of 5-bromo-2-benzofuranyl methyl ketone and p-chlorobenzaldehyde in methanol solution in the presence of aqueous sodium hydroxide. The starting material melts at 183°–185° C.

EXAMPLE 17

Preparation of the (1,4,5,6-Tetrahydro-2-pyrimidinyl)hydrazone of 1-(5-Phenyl-2-benzofuranyl)-3-(p-chlorophenyl)-2-propen-1-one hydrochloride A mixture of 7.18 g. of 1-(5-phenyl-2-benzofuranyl)-3-(p-chlorophenyl)-2-propen-1-one and 3.02 g. of 2-hydrazino-1,4,5,6-tetrahydropyrimidine hydrochloride in 150 ml. of n-propanol containing 5 drops of concentrated hydrochloric acid is boiled for 2 hours and concentrated to about 75 ml. After cooling, a cream colored precipitate forms which is filtered, washed with n-propanol and dried yielding 6.5 g., m.p. 203°–205° C.

Analysis calculated for $C_{27}H_{23}N_4OCl$ . HCl: C, 65.99; H, 4.93; N, 11.40; Cl, 14.43. Found: C, 64.15; H, 4.75; N, 11.10; Cl, 14.12.

The starting material 1-(5-phenyl-2-benzofuranyl)-3-(p-chlorophenyl)-2-propen-1-one is prepared by the reaction of 2-acetyl-5-phenyl benzofuran and 4-chlorobenzaldehyde in methanol solution in the presence of aqueous sodium hydroxide. The starting material melts at 180°–182° C.

EXAMPLE 18

Preparation of the (1,4,5,6-Tetrahydro-2-pyrimidinyl)hydrazone of 1-(7-Methoxy-2-benzofuranyl)-3-(p-chlorophenyl)-2-propen-1-one hydrochloride A mixture of 6.26 g. of 1-(7-methoxy-2-benzofuranyl)-3-(p-chlorophenyl)-2-propen-1-one and 3.02 g. of 2-hydrazino-1,4,5,6-tetrahydropyrimidine hydrochloride in 150 ml. of n-propanol containing 4 drops of concentrated hydrochloric acid is boiled for 1.5 hours, concentrated to about 50 ml. and cooled yielding a solid. This solid is filtered, washed with n-propanol and dried yielding a pale yellow solid, 5.7 g., m.p. 243°–245° C.

Analysis calculated for $C_{22}H_{21}N_4O_2Cl$ . HCl: C, 59.32; H, 4.98; N, 12.58; Cl, 15.93. Found: C, 58.78; H, 5.41; N, 12.35; Cl, 15.47.

The starting material 1-(7-methoxy-2-benzofuranyl)-3-(p-chlorophenyl)-2-propen-1-one is prepared by the reaction of 7-methoxy-2-benzofuranyl methyl ketone and p-chlorophenyl benzaldehyde in methanol solution in the presence of aqueous sodium hydroxide. The starting material melts at 148°–151° C.

EXAMPLE 19

Preparation of the (1,4,5,6-Tetrahydro-2-pyrimidinyl)hydrazone of 1-(5-Methoxy-2-benzofuranyl)-3-(p-chlorophenyl)-2-propen-1-one A mixture of 6.26 g. of 1-(5-methoxy-2-benzofuranyl)-3-(p-chlorophenyl)-2-propen-1-one and 3.02 g. of 2-hydrazino-1,4,5,6-tetrahydropyrimidine hydrochloride in 150 ml. of n-propanol containing 4 drops of concentrated hydrochloric acid is heated to boiling and then cooled overnight. This solution is basified with saturated sodium bicarbonate solution and diluted with 4 volumes of water producing a gum. This gum is filtered, washed with water, dried and recrystallized from 100 ml. of n-propanol yielding a bright yellow solid, 4.6 g., m.p. 182°–183° C.

The starting material 1-(5-chloro-2-benzofuranyl)-3-(p-chlorophenyl)-2-propen-1-one is prepared by the reaction of 5-chloro-2-acetylbenzofuran and p-chlorobenzaldehyde in methanol solution in the presence of aqueous sodium hydroxide. The starting material melts at 171°–175° C.

Analysis calculated for $C_{22}H_{21}N_4O_2Cl$: C, 64.62; H, 5.18; N, 13.70; Cl, 8.67. Found: C, 64.77; H, 5.42; N, 13.72; Cl, 8.76.

The starting material 1-(5-methoxy-2-benzofuranyl)-3-(p-chlorophenyl)-2-propen-1-one is prepared by the reaction of 5-methoxy-2-benzofuranyl methyl ketone and p-chlorobenzalhyde in methanol solution in the presence of aqueous sodium hydroxide. The starting material melts at 138°–139° C.

EXAMPLE 20

Preparation of the (1,4,5,6-Tetrahydro-2-pyrimidinyl)hydrazone of 1-(5-Methyl-2-benzofuranyl)-3-(p-chlorophenyl)-2-propen-1-one methylate A mixture of 11 g. of 1-(5-methyl-2-benzofuranyl)-3-(p-chlorophenyl)-2-propen-1-one and 5.6 g. of 2-hydrazino-1,4,5,6-tetrahydropyrimidine hydrochloride in n-propanol is refluxed for 2–3 hours with periodic additions of concentrated hydrochloric acid. The mixture is concentrated to 50 ml., cooled basified with saturated sodium bicarbonate solution and diluted to 250 ml. The gum which forms is washed with water and dissolved in 350 ml. of boiling methanol, filtered and then cooled yielding 10.2 g. of yellow grains, m.p. 160°–162° C.

Analysis calculated for $C_{22}H_{21}N_4OCl \cdot OCH_3$: C, 65.03; H, 5.93; N, 13.20; Cl, 8.34. Found: C, 65.16; H, 6.09; N, 13.47; Cl, 8.37.

The starting material 1-(5-methyl-2-benzofuranyl)-3-(p-chlorophenyl)-2-propen-1-one is prepared by the reaction of 5-methyl-2-benzofuranyl methyl ketone and p-chlorobenzaldehyde in methanol solution in the presence of aqueous sodium hydroxide. The starting material melts at 175°–176° C.

EXAMPLE 21

Preparation of the (1,4,5,6-Tetrahydro-2-pyrimidinyl)hydrazone of 1-(1,3-Dioxolo[4,5-f][1]benzofuran-6-yl)-3-(p-chlorophenyl)-2-propen-1-one hydrochloride, n-propanolate A mixture of 6.6. g. of 1-(1,3-dioxolo[4,5-f][1]benzofuran-6-yl)-3-(p-chlorophenyl)-2-propen-1-one and 3.0 g. of 2-hydrazino-1,4,5,6-tetrahydropyrimidine hydrochloride in 150 ml. of n-propanol containing 5 drops of concentrated hydrochloric acid is boiled for 2 hours, concentrated to 50 ml. and cooled giving a yellow solid. This solid is washed with n-propanol, dried and recrystallized from 200 ml. of n-propanol containing activated charcoal, yielding 8.0 g., m.p. 180°–183° C.

Analysis calculated for $C_{22}H_{19}N_4O_3Cl \cdot HCl \cdot C_3H_7OH$: C, 57.80; H, 5.43; N, 10.79; Cl, 13.65. Found: C, 57.67; H, 5.67; N, 10.58; Cl, 13.40.

The starting material 1-(1,3-dioxolo[4,5-f][1]benzofuran-6-yl)-3-(p-chlorophenyl)-2-propen-1-one is prepared by the reaction of 2-acetyl-5,6-methylenedioxy benzofuran and p-chlorobenzaldehyde in methanol solution in the presence of aqueous sodium hydroxide. The starting material melts at 243°–245° C.

EXAMPLE 22

Preparation of the (1,4,5,6-Tetrahydro-2-pyrimidinyl)hydrazone of 1-(3-Phenyl-2-benzofuranyl)-3-(p-chlorophenyl)-2-propen-1-one The procedure of Example 5 is followed employing 7.2 g. of 1-(3-phenyl-2-benzofuranyl)-3-(p-chlorophenyl)-2-propen-1-one (prepared as described in Example 18) and 3.1 g. of 2-hydrazino-1,4,5,6-tetrahydropyrimidine hydrochloride. The concentrated n-propanol mixture is filtered while hot through diatomaceous earth and then cooled yielding 2.0 g. of a yellow solid, m.p. 115°–117° C.

Analysis calculated for $C_{27}H_{23}N_4OCl$: C, 71.27; H, 5.10; N, 12.31; Cl, 7.79. Found: C, 71.09; H, 5.11; N, 11.14; Cl, 7.41.

EXAMPLE 23

Preparation of the (1,4,5,6-Tetrahydro-2-pyrimidinyl)hydrazone of 1-(5-Methyl-2-benzofuranyl)-3-(p-methoxyphenyl)-2-propen-1-one hydrochloride A mixture of 4.5 g. of 1-(5-methyl-2-benzofuranyl)-3-(p-methoxyphenyl)-2-propen-1-one and 3.0 g. of 2-hydrazino-1,4,5,6-tetrahydropyrimidine hydrochloride in 60 ml. of n-propanol is boiled for 40 minutes and then concentrated to dryness. The residue is dissolved in benzene and filtered. On cooling a yellow solid crystallizes which is collected, washed with benzene and n-propanol 4.0 g., m.p. 213°–216° C.

Analysis calculated for $C_{23}H_{24}N_4O_2 \cdot HCl$: C, 65.0; H, 5.9; N, 13.2, Cl, 8.3. Found: C, 64.6; H, 6.1; N, 13.3; Cl, 8.9.

The starting material 1-(5-methyl-2-benzofuranyl)-3-(p-methoxyphenyl)-2-propen-1-one is prepared by the reaction of 5-methyl-2-benzofuranyl methyl ketone and p-anisaldehyde in methanol solution in the presence of aqueous sodium hydroxide. The starting material melts at 136°–137° C.

EXAMPLE 24

Preparation of the (1,4,5,6-Tetrahydro-2-pyrimidinyl)hydrazone of 1-(5-Chloro-3-methyl-2-benzofuranyl)-3-(p-chlorophenyl)-2-propen-1-one hydrochloride A mixture of 9.93 g. of 1-(5-chloro-3-methyl-2-benzofuranyl)-3-(p-chlorophenyl)-2-propen-1-one and 4.52 g. of 2-hydrazino-1,4,5,6-tetrahydropyrimidine hydrochloride in 150 ml. of n-propanol containing 6 drops of concentrated hydrochloric acid is boiled for 2 hours. The yellow solid is removed by filtration, washed with n-propanol and dried. This solid is recrystallized from 225 ml. of n-propanol yielding 5.6 g. of yellow crystals, m.p. 260°–265° C.

Analysis calculated for $C_{21}H_{20}N_4Cl_2O \cdot HCl$: C, 56.97; H, 4.56; N, 12.08; Cl, 22.93. Found: C, 57.30; H, 4.60; N, 11.50; Cl, 22.34.

The starting material 1-(5-chloro-3-methyl-2-benzofuranyl)-3-(p-chlorophenyl)-2-propen-1-one is prepared by the reaction of 3-methyl-5-chlorobenzofuran-2-yl methyl ketone and p-chlorobenzaldehyde in methanol solution in the presence of aqueous sodium hydroxide. The starting material melts at 170°–172° C.

EXAMPLE 25

Preparation of the
(1,4,5,6-Tetrahydro-2-pyrimidinyl)hydrazone of
1,3-Bis(5-chloro-2-benzofuranyl)-2-propen-1-one A mixture of 3.57 g. of 1,3-bis(5-chloro-2-benzofuranyl)-2-propen-1-one and 1.51 g. of 2-hydrazino-1,4,5,6-tetrahydropyrimidine hydrochloride in 150 ml. of n-propanol containing 5 drops of concentrated hydrochloric acid is boiled for 2 hours, cooled and then filtered. The filtrate is basified with saturated sodium bicarbonate solution and diluted with 3 volumes of water yielding a solid. This solid is dissolved in 200 ml. of methanol, filtered and boiled until the product forms as orange crystals, 1.2 g., m.p. 162°–164° C.

Analysis calculated for $C_{23}H_{18}N_4Cl_2O_2$: C, 60.94; H, 4.02; N, 12.36; Cl, 15.64. Found: C, 60.83; H, 4.15; N, 12.17; Cl, 15.83.

The starting material 1,3-bis(5-chloro-2-benzofuranyl)-2-propen-1-one is prepared by the reaction of 5-chlorobenzofuran-2-yl methyl ketone and 5-chlorobenzofuran-2-yl carboxaldehyde in methanol solution in the presence of aqueous sodium hydroxide. The starting material melts at 225°–227° C.

EXAMPLE 26

Preparation of the 2-Imidazolin-2-ylhydrazone of
1-(5-Chloro-2-benzofuranyl)-3-[p-(methylthio)-
phenyl]-2-propen-1-one hydrochloride A mixture of 3.3 g. of 1-(5-chloro-2-benzofuranyl)-3-[p-(methylthio)phenyl]-2-propen-1-one and 1.9 g. of 2-hydrazino-2-imidazoline hydrochloride in 100 ml. of n-propanol is boiled for 1 hour, filtered and concentrated to a gum. The gum is dissolved in chloroform, filtered and concentrated with the addition of benzene to obtain a gum. The benzene is decanted and the gum is triturated with ethanol producing a white solid which is collected by filtration, washed with ethanol and ether yielding 1.54 g., m.p. 236°–237° C.

Analysis calculated for $C_{21}H_{19}ClN_4OS \cdot HCl$: C, 56.38; H, 4.50; Cl, 15.85; N, 12.52; S, 7.17. Found: C, 56.13; H, 4.58; Cl, 16.14; N, 12.68; S, 6.75.

The starting material 1-(5-chloro-2-benzofuranyl)-3-[p-(methylthio)phenyl]-2-propen-1-one is prepared by the reaction of 5-chloro-2-benzofuranyl methyl ketone with p-(methylthio)benzaldehyde in isopropanol solution containing hydrogen chloride as catalyst. This ketone melts at 162°–163° C.

EXAMPLE 27

Preparation of the
(1,4,5,6-Tetrahydro-2-pyrimidinyl)hydrazone of
1-(5-Chloro-2-benzofuranyl)-3-m-tolyl-2-propen-
1-one hydrochloride A mixture of 4.45 g. of 1-(5-chloro-2-benzofuranyl)-3-m-tolyl-2-propen-1-one and 2.9 g. of 2-hydrazino-1,4,5,6-tetrahydropyrimidine hydrochloride in 40 ml. of n-propanol is boiled for 50 minutes and then concentrated. The residue is dissolved in chloroform which is then removed and replaced with benzene and then a mixture of ether and n-propanol. The pale yellow crystals which form are washed with n-propanol and ether yielding 3.06 g., m.p. 218.5°–219.5° C.

Analysis calculated for $C_{22}H_{21}N_4OCl \cdot HCl \cdot \frac{1}{3}H_2O$: C, 60.70; H, 5.25; N, 12.87; Cl, 16.29. Found: C, 60.53; H, 5.10; N, 13.25; Cl, 16.34.

The starting material 1-(5-chloro-2-benzofuranyl)-3-m-tolyl-2-propen-1-one is prepared by reacting 5-chloro-2-benzofuranyl methyl ketone with m-tolualdehyde in isopropanol solution containing hydrogen chloride as catalyst. This ketone melts at 151.5°–152.5° C.

EXAMPLE 28

Preparation of the
(1,4,5,6-Tetrahydro-2-pyrimidinyl)hydrazone of
1-(5-Chloro-2-benzofuranyl)-3-(3,5-xylyl)-2-propen-
1-one hydrochloride A mixture of 4.7 g. of 1-(5-chloro-2-benzofuranyl)-3-(3,5-xylyl)-2-propen-1-one and 3.0 g. of 2-hydrazino-1,4,5,6-tetrahydropyrimidine hydrochloride in 50 ml. of n-propanol and 30 ml. of benzene is boiled for 1 hour, concentrated to about 20 ml. and 5 ml. of ether is added. The pale yellow crystals are washed with n-propanol and ether yielding 4.70 g., m.p. 239°–240° C.

Analysis calculated for $C_{23}H_{23}OClN_4 \cdot HCl \cdot \frac{1}{3}H_2O$: C, 61.48; H, 5.53; N, 12.47; Cl, 15.78. Found: C, 61.41; H, 5.35; N, 12.49; Cl, 15.94.

The starting material 1-(5-chloro-2-benzofuranyl)-3-(3,5-xylyl)-2-propen-1-one is prepared by reacting 5-chloro-2-benzofuranyl methyl ketone with 3,5-dimethylbenzaldehyde in isopropanol solution containing hydrogen chloride as catalyst. This ketone melts at 122.5°–123.5° C.

EXAMPLE 29

Preparation of the
(1,4,5,6-Tetrahydro-2-pyrimidinyl)hydrazone of
1-(5,7-Dichloro-2-benzofuranyl)-3-(p-chlorophenyl)-
2-propen-1-one A mixture of 3.51 g. of 1-(5,7-dichloro-2-benzofuranyl)-3-(p-chlorophenyl)-2-propen-1-one and 1.51 g. of 2-hydrazino-1,4,5,6-tetrahydropyrimidine hydrochloride in 100 ml. of n-propanol containing 5 drops of concentrated hydrochloric acid is boiled for 1 hour, concentrated to about 75 ml. and filtered. The filtrate is treated with 2 volumes of water and basified with saturated sodium bicarbonate solution. The bright yellow precipitate is washed with water and then boiled in 100 ml. of n-propanol. On cooling an orange solid forms. Concentration of the mother liquor gives additional solid. The combined solids are dissolved in 25 ml. of boiling chloroform, filtered and cooled, yielding bright yellow crystals 0.5 g., m.p. 232°–233° C.

Analysis calculated for $C_{21}H_{17}N_4OCl_3$: C, 56.33; H, 3.83; N, 12.52; Cl, 23.76. Found: C, 56.19; H, 3.90; N, 12.67; Cl, 24.22.

The starting material 1-(5,7-dichloro-2-benzofuranyl)-3-(p-chlorophenyl)-2-propen-1-one is prepared by the reaction of 5,7-dichlorobenzofuran-2-yl methyl ketone and p-chlorobenzaldehyde in methanol solution in the presence of sodium hydroxide. The starting material melts at 90°–91° C.

EXAMPLE 30

Preparation of the
(4-Methyl-2-imidazolin-2-yl)hydrazone of
1-(2-Benzofuranyl)-3-(p-chlorophenyl)-2-propen-
1-one A mixture of 2.83 g. of 1-(2-benzofuranyl)-3-(p-chlorophenyl)-2-propen-1-one prepared as described in Example 5 and 1.87 g. of 2-hydrazino-4-methyl-2-imidazoline dihydrochloride in 75 ml. of n-propanol is boiled for 1 hour, concentrated to about 40 ml. and cooled. The concentrate is diluted with 3 volumes of water and basified with saturated sodium bicarbonate solution. The gum which forms is washed twice with water and dissolved in 75 ml. of methanol and concentrated by boiling to 50 ml. The solid which forms is recrystallized from ethanol yielding 1.0 g., m.p. 182°–184° C.

Analysis calculated for $C_{21}H_{19}N_4OCl$: C, 66.75; H, 5.17; N, 14.83; Cl, 9.39. Found: C, 66.61; H, 5.19; N, 14.51; Cl, 9.39.

EXAMPLE 31

Preparation of the 4,5,6,7-Tetrahydro-1H-1,3-diazepin-2-ylhydrazone of 1-(5-Chloro-2-benzofuranyl)-3-(p-chlorophenyl)-2-propen-1-one A mixture of 3.17 g. of 1-(5-chloro-2-benzofuranyl)-3-(p-chlorophenyl)-2-propen-1-one (prepared as described in Example 15) and 2.01 g. of 2-hydrazino-4,5,6,7-tetrahydro-1H-1,3-diazepine hydrochloride in 75 ml. of n-propanol is boiled for 1 hour and concentrated to 50 ml. The supernatant is diluted with 3 volumes of water and basified with sodium bicarbonate solution. The light yellow solid is washed with water and boiled in 100 ml. of ethanol. On cooling a yellow solid forms which is washed with ethanol and dried yielding 2.5 g., m.p. 210°–212° C.

Analysis calculated for $C_{22}H_{20}N_4OCl_2$: C, 61.83; H, 4.72; N, 13.11; Cl, 16.60. Found: C, 61.29; H, 4.86; N, 13.21; Cl, 16.53.

EXAMPLE 32

Preparation of the (1,4,5,6-Tetrahydro-5-pyrimidinyl)hydrazone of 1-(2-Benzofuranyl)-3-(p-chlorophenyl)-2-propen-1-one A mixture of 2.82 g. of 1-(2-benzofuranyl)-3-(p-chlorophenyl)-2-propen-1-one (prepared as described in Example 5) and 1.51 g. of 2-hydrazino-1,4,5,6-tetrahydropyrimidine hydrochloride in 75 ml. of n-propanol is treated as described in Example 31. After basification the product hardens, is filtered, washed with water and dried. This solid is recrystallized from 250 ml. of ethanol yielding 2.3 g. of yellow solid, m.p. 182°–184° C.

Analysis calculated for $C_{21}H_{19}N_4OCl$: C, 66.75; H, 5.17; N, 14.83; Cl, 9.39. Found: C, 66.58; H, 5.21; N, 14.77; Cl, 9.58.

EXAMPLE 33

Preparation of the (1,4,5,6-Tetrahydro-2-pyrimidinyl)hydrazone of 1-(5-Chloro-2-benzofuranyl)-3-(4-biphenylyl)-2-propen-1-one A mixture of 5.3 g. of 1-(5-chloro-2-benzofuranyl)-3-(4-biphenylyl)-2-propen-1-one and 2.9 g. of 2-hydrazino-1,4,5,6-tetrahydropyrimidine dihydrochloride in 100 ml. of n-propanol is heated to boiling for 1 hour and concentrated giving a gummy solid. This solid is extracted with chloroform from aqueous alkaline, washed and dried to a gum. This gum is crystallized from a benzene-methanol mixture and purified by passing through an alumina column, eluting with chloroform. The product is crystallized from a mixture of chloroform and methanol as yellow crystals, 3.52 g., m.p. 208°–209° C.

Analysis calculated for $C_{27}H_{23}N_4OCl$: C, 71.28; H, 5.10; N, 12.31. Found: C, 71.06; H, 5.26; N, 12.04.

The starting material 1-(5-chloro-2-benzofuranyl)-3-(4-biphenylyl)-2-propen-1-one is prepared by reacting 5-chloro-2-benzofuranyl methyl ketone with 4-biphenylcarboxaldehyde in isopropanol solution containing hydrogen chloride catalyst. This ketone melts at 204°–205° C.

EXAMPLE 34

Preparation of the 2-Imidazolin-2-ylhydrazone of 1-(5-Methyl-2-benzofuranyl)-3-(p-chlorophenyl)-2-propen-1-one A mixture of 3 g. of 1-(5-methyl-2-benzofuranyl)-3-(p-chlorophenyl)-2-propen-1-one (prepared as described in Example 20) and 1.73 g. of 2-hydrazino-2-imidazolidine dihydrochloride in n-propanol is treated as described in Example 18. The solidified oil is boiled in 100 ml. of methanol and cooled. The solid is washed with methanol and dried yielding 2.0 g., m.p. 202°–204° C.

Analysis calculated for $C_{21}H_{19}N_4OCl$: C, 66.57; H, 5.05; N, 14.78; Cl, 9.36. Found: C, 65.88; H, 5.19; N, 14.67; Cl, 9.31.

EXAMPLE 35

Preparation of the (1,4,5,6-Tetrahydro-2-pyrimidinyl)hydrazone of 1-(5-Methyl-2-benzofuranyl)-3-(3,5-xylyl)-2-propen-1-one A mixture of 4.80 g. of 1-(5-methyl-2-benzofuranyl)-3-(3,5-xylyl)-2-propen-1-one and 3.2 g. of 2-hydrazino-1,4,5,6-tetrahydropyrimidine dihydrochloride in 100 ml. of n-propanol is boiled for 30 minutes, cooled and concentrated. The residue is extracted with chloroform, dried, concentrated and crystallized from ether yielding 4.26 g. of yellow crystals, m.p. 142.5°–143.5° C.

Analysis calculated as $C_{24}H_{26}N_4O$: C, 74.58; H, 6.78; N, 14.50. Found: C, 74.16; H, 7.17; N, 14.24.

The starting material 1-(5-methyl-2-benzofuranyl)-3-(3,5-xylyl)-2-propen-1-one is prepared by reacting 5-chloro-2-benzofuranyl methyl ketone with 3,5-dimethylbenzaldehyde in isopropanol solution containing hydrogen chloride catalyst. This ketone melted at 156°–157° C.

EXAMPLE 36

Preparation of the 4,5,6,7-Tetrahydro-1H-1,3-diazepin-2-ylhydrazone of 1-(5-Methyl-2-benzofuranyl)-3-(p-chlorophenyl)-2-propen-1-one A mixture of 3 g. of 1-(5-methyl-2-benzofuranyl)-3-(p-chlorophenyl)-2-propen-1-one (prepared as described in Example 20) and 2 g. of 2-hydrazino-4,5,6,7-tetrahydro-1H-1,3-diazepine dihydrochloride is treated as described in Example 35. The yellow solid is boiled in 100 ml. of methanol, cooled, filtered, washed with methanol and dried. This solid is recrystallized from ethanol yielding 2.0 g. of yellow solid, m.p. 183°–185° C.

Analysis calculated for $C_{23}H_{23}N_4OCl$: C, 67.89; H, 5.70; N, 13.77; Cl, 8.71. Found: C, 68.12; H, 6.06; N, 13.50; Cl, 8.64.

EXAMPLE 37

Preparation of the (1,4,5,6-Tetrahydro-2-pyrimidinyl)hydrazone of 1-(5-tert-Butyl-2-benzofuranyl)-3-p-chlorophenyl)-2-propen-1-one A mixture of 6.8 g. of 1-(5-tert-butyl-2-benzofuranyl)-3-(p-chlorophenyl)-2-propen-1-one and 3.02 g. of 2-hydrazino-1,4,5,6-tetrahydropyrimidine hydrochloride in 100 ml. of n-propanol containing 5 drops of concentrated hydrochloric acid is boiled and concentrated over a 1-2 hour period to 50 ml. The mixture is diluted to 200 ml. with water and basified with sodium bicarbonate solution yielding a yellow gum which is dissolved in 100 ml. of boiling methanol, filtered and cooled. This solution is treated with 3 volumes of water giving a yellow precipitate which is dissolved in 200 ml. of hot methanol, filtered and cooled yielding 2.3 g. of yellow solid, m.p. 136°–138° C.

Analysis calculated for $C_{25}H_{27}N_4OCl$: C, 69.02; H, 6.26; N, 12.88; Cl, 8.15. Found: C, 68.75; H, 6.28; N, 12.27; Cl, 8.12.

The starting material 1-(5-tert-butyl-2-benzofuranyl-3-(p-chlorophenyl)-2-propen-1-one is prepared by the reaction of 5-t-butylbenzofuran-2-yl methyl ketone and p-chlorobenzaldehyde in methanol solution in the presence of aqueous sodium hydroxide. The starting material melts at 174°–176° C.

EXAMPLE 38

Preparation of the (1,4,5,6-Tetrahydro-2-pyrimidinyl)hydrazone of 1-(5-Chloro-2-benzofuranyl)-3-[p-(methylthio)phenyl]-2-propen-1-one hydrochloride A mixture of 3.90 g. of 1-(5-chloro-2-benzofuranyl)-3-[p-(methylthio)phenyl]-2-propen-1-one (prepared as described in Example 26) and 2.6 g. of 2-hydrazino-1,4,5,6-tetrahydropyrimidine dihydrochloride in 50 ml. of n-propanol is boiled for 40 minutes and concentrated to about 20 ml. yielding yellow crystals which are filtered and then dissolved in chloroform. This solution is then concentrated and benzene is added yielding yellow crystals. This product is recrystallized from chloroform while adding n-propanol and removing chloroform yielding 4.0 g., m.p. 204°–206° C.

Analysis calculated for $C_{22}H_{21}N_4SOCl \cdot HCl \cdot \frac{1}{2}H_2O$: C, 56.17; H, 4.93; N, 11.91; Cl, 15.07; S, 6.81. Found: C, 56.02; H, 4.99; N, 12.01; Cl, 15.10; S, 6.57.

EXAMPLE 39

Preparation of the (1,4,5,6-Tetrahydro-2-pyrimidinyl)hydrazone of 1-(5,7-Dimethyl-2-benzofuranyl)-3-(p-chlorophenyl)-2-propen-1-one A mixture of 6.2 g. of 1-(5,7-dimethyl-2-benzofuranyl)-3-(p-chlorophenyl)-2-propen-1-one and 3.02 g. of 2-hydrazino-1,4,5,6-tetrahydropyrimidine hydrochloride is refluxed in 100 ml. of n-propanol containing 5 drops of concentrated hydrochloric acid for 3 hours and concentrated to 50 ml. On cooling a pale yellow solid forms which is washed with n-propanol and then recrystallized from n-propanol. This solid is stirred in an excess of sodium bicarbonate solution, filtered, washed with water and dried. This solid is dissolved in 150 ml. of methanol, clarified, treated with excess sodium bicarbonate solution and water yielding 1.5 g. of light yellow solid, m.p. 115°–117° C.

Analysis calculated for $C_{23}H_{23}N_4ClO$: C, 67.89; H, 5.70; N, 13.77; Cl, 8.71. Found: C, 67.59; H, 5.71; N, 13.58; Cl, 8.67.

The starting material 1-(5,7-dimethyl-2-benzofuranyl)-3-(p-chlorophenyl)-2-propen-1-one is prepared by the reacting of 5,7-dimethylbenzofuran-2-yl methyl ketone and p-chlorobenzaldehyde in methanol solution in the presence of aqueous sodium hydroxide. The starting material melts at 110°–112° C.

EXAMPLE 40

Preparation of the (1,4,5,6-Tetrahydro-2-pyrimidinyl)hydrazone of 1-(3-Methyl-5,7-dimethoxy-2-benzofuranyl)-3-p(-chlorophenyl)-2-propen-1-one hydrochloride n-propanolate A mixture of 8.95 g. of 1-(3-methyl-5,7-dimethoxy-2-benzofuranyl)-3-(p-chlorophenyl)-2-propen-1-one and 3.77 g. of 2-hydrazino-1,4,5,6-tetrahydropyrimidine hydrochloride in 150 ml. of n-propanol containing 5 drops of concentrated hydrochloric acid is boiled for 2 hours, filtered and then cooled yielding 4.0 g. of yellow solid, m.p. 230°–233° C.

Analysis calculated for $C_{24}H_{25}N_4O_3Cl \cdot HCl$: C, 58.89; H, 5.36; N, 11.45; Cl, 14.49. Found: C, 58.54; H, 5.59; N, 9.64; Cl, 13.21.

The starting material 1-(3-methyl-5,7-dimethoxy-2-benzofuranyl)-3-(p-chlorophenyl)-2-propen-1-one is prepared by the reaction of 3-methyl-5,7-dimethoxybenzofuran-2-yl methyl ketone and p-chlorobenzaldehyde in methanol solution in the presence of aqueous sodium hydroxide. The starting material melts at 127°–128° C.

EXAMPLE 41

Preparation of the (1,4,5,6-Tetrahydro-2-pyrimidinyl)hydrazone of 1-(5-Isopropyl-2-benzofuranyl)-3-(p-chlorophenyl)-2-propen-1-one A mixture of 9.75 g. of 1-(5-isopropyl-2-benzofuranyl)-3-(p-chlorophenyl)-2-propen-1-one and 4.5 g. of 2-hydrazino-1,4,5,6-tetrahydropyrimidine hydrochloride in 300 ml. of n-propanol containing 5 drops of concentrated hydrochloric acid is boiled for 3 hours and concentrated to 150 ml. The mixture is cooled, poured into 700 ml. of water and basified with excess sodium bicarbonate solution. The gum which forms is filtered, washed with water and dissolved in 350 ml. of methanol, yielding a yellow oil. The supernatant is poured off and cooled giving a yellow-orange precipitate 1.1 g., m.p. 113°–115° C.

Analysis calculated for $C_{24}H_{25}N_4OCl$: C, 68.47; H, 5.99; N, 13.31; Cl, 8.42. Found: C, 68.12; H, 5.96; N, 12.67; Cl, 8.12.

The starting material 1-(5-isopropyl-2-benzofuranyl)-3-(p-chlorophenyl)-2-propen-1-one is prepared by the reaction of 5-isopropylbenzofuran-2-yl methyl ketone and p-chlorobenzaldehyde in methanol solution in the presence of aqueous sodium hydroxide solution. The starting material melts at 140°–142° C.

We claim:
1. A method for the treatment of tubercular infections in a warm-blooded animal which comprises ad- ministering to said animal an anti-tubercular effective amount of an anti-tubercular agent of the formula:

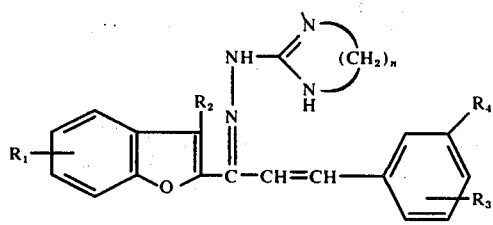

wherein $R_1$ and $R_3$ may be the same or different and are selected from the group consisting of hydrogen, chloro, bromo, fluoro, $C_1-C_4$ alkoxy, phenyl, $C_1-C_4$ alkyl, and $C_1-C_4$ alkyl thio, $R_2$ is selected from the group consisting of hydrogen, $C_1-C_4$ alkyl and phenyl, $R_4$ is hydrogen, $C_1-C_4$ alkyl or chloro and when $R_3$ and $R_4$ are present on adjacent carbon atoms, they may represent $-O-CH_2-O-$, $n$ is 2, 3 or 4 or an acid addition salt thereof.

2. A method in accordance with claim 1, wherein the anti-tubercular agent is administered at the rate of 10 mg. to about 500 mg. per day.

3. The method in accordance with claim 1, wherein the anti-tubercular agent is (1,4,5,6-tetrahydro-2-pyrimidinyl)hydrazone of 1-(5-chloro-2-benzofuranyl)-3-(p-chlorophenyl)-2-propen-1-one.

4. A composition for controlling tubercular infections in a warm-blooded animal which comprises a pharmaceutically acceptable carrier and from 10 mg. to 500 mg. of an anti-tubercular agent of the formula:

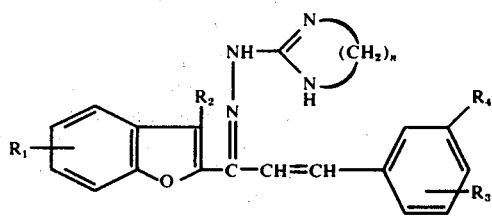

wherein $R_1$ and $R_3$ may be the same or different and are selected from the group consisting of hydrogen, chloro, bromo, fluoro, $C_1-C_4$ alkoxy, phenyl, $C_1-C_4$ alkyl, and $C_1-C_4$ alkyl thio, $R_2$ is selected from the group consisting of hydrogen, $C_1-C_4$ alkyl and phenyl, $R_4$ is hydrogen, $C_1-C_4$ alkyl or chloro and when $R_3$ and $R_4$ are present on adjacent carbon atoms, they may represent $-O-CH_2-O-$, $n$ is 2, 3 or 4 or an acid addition salt thereof.

* * * * *